United States Patent [19]
Danforth et al.

[11] Patent Number: 5,192,295
[45] Date of Patent: Mar. 9, 1993

[54] ANGIOPLASTY DILATATION BALLOON CATHETER/GUIDEWIRE SYSTEM

[75] Inventors: John W. Danforth, San Francisco; Jeff L. Kraus; Michael J. Horzewski, both of San Jose; Hugh R. Sharkey, San Francisco, all of Calif.

[73] Assignee: Danforth Biomedical, Inc., Menlo Park, Calif.

[21] Appl. No.: 540,957

[22] Filed: Jun. 20, 1990

[51] Int. Cl.⁵ .................................... A61M 29/00
[52] U.S. Cl. .................................... 606/194; 604/96; 128/772
[58] Field of Search ............... 128/656–658, 128/772; 604/96, 280, 99, 164; 606/191–192, 194

[56] References Cited

U.S. PATENT DOCUMENTS

| | | | |
|---|---|---|---|
| 4,342,315 | 8/1982 | Jackson | 604/280 X |
| 4,545,390 | 10/1985 | Leary | 128/772 |
| 4,932,959 | 6/1990 | Horzewski et al. | 606/194 |
| 4,988,356 | 1/1991 | Crittenden et al. | 606/192 |
| 5,002,559 | 3/1991 | Tower | 606/194 |
| 5,085,636 | 2/1992 | Burns | 604/99 |
| 5,106,368 | 4/1992 | Uldall et al. | 604/43 |

FOREIGN PATENT DOCUMENTS

| | | | |
|---|---|---|---|
| 0246998 | 11/1987 | European Pat. Off. | 606/192 |
| 0254701 | 1/1988 | European Pat. Off. | |
| 0266957 | 5/1988 | European Pat. Off. | |
| 2581882 | 11/1986 | France | 606/192 |
| WO8905609 | 6/1989 | World Int. Prop. O. | |

*Primary Examiner*—C. Fred Rosenbaum
*Assistant Examiner*—C. Maglione

[57] ABSTRACT

An angioplasty catheter system is disclosed which allows insertion and removal of a guidewire through the inner member of the catheter, yet which inner member includes a portion which is smaller than the cross-section of portions of the guidewire. Advancement and removal of the guidewire are achieved by forming the first portion of the inner member of the catheter shaft from material which is expandable, or which is sufficiently thin to be folded and temporarily secured in place using several techniques.

13 Claims, 9 Drawing Sheets

ANGIOPLASTY DILATATION BALLOON CATHETER/GUIDEWIRE SYSTEM

BACKGROUND OF THE INVENTION

This invention relates to catheters and in particular to guidewire-directed dilation balloon catheters, for use in the performance of percutaneous transluminal peripheral and coronary angioplasty.

In 1977 Dr. Andreas Gruentzig first used a balloon-tipped flexible catheter to percutaneously dilate a region of stenosis within the coronary artery of a patient with atherosclerotic heart disease. Since that time, the incidence of percutaneous transluminal coronary angioplasty has increased exponentially. Over the course of the past eight to ten years, the performance of this procedure has become routine within many major medical centers throughout the world. With the advent of improved technology and operator skill, the indications for this procedure have increased substantially.

U.S. Pat. No. 4,195,637 describes the original catheter conceived by Dr. Gruentzig. By current standards, the design of this device affords limited directional control. Use of this device was largely abandoned in the early 1980's following the introduction of "over-the-wire" catheters. U.S. Pat. No. 4,299,226, describes an over-the-wire catheter. Over-the-wire catheters have remained the most popular angioplasty catheters to date, despite the advent of a variety of more recently developed "non-over-the-wire" catheter systems. The popularity of over-the-wire catheters stems largely from the fact that these catheters remain the safest and, with minor exception, the most steerable catheters among the prior art.

The primary limitation of the various over-the-wire catheters of the prior art concerns their respective crossing profiles. For the purposes of this discussion, the crossing profile of a balloon catheter system is defined as the maximal profile of the deflated balloon component of the system. Relative to the more recently developed non-over-the-wire devices, over-the-wire devices have substantially larger crossing profiles. Hence, these catheters create more resistance during manipulation within the confines of critical stenoses, require more force to install across lesions and cause more intravascular trauma during this process compared to the more recently developed, lower profile non-over-the-wire devices.

Considerable effort has been directed toward the development of over-the-wire systems with progressively lower crossing profiles. Virtually all of the progress to date, however, has resulted from progressive miniaturization of the components contained within these devices. The use of state-of-the-art plastics has permitted the manufacture of these devices with progressively thinner walls, and the development of new technologies has permitted the construction of these devices with progressively smaller caliber lumens. Relatively little benefit has resulted from efforts to modify the fundamental design of over-the-wire devices which has remained essentially unchanged to date.

The factors that influence the magnitude of the crossing profile of an over-the-wire device of the prior art include: (1) the inflated profile of the balloon component, (2) the thickness of the walls of the balloon component and (3) the profile of the inner member that extends through the confines of the balloon component.

The first factor, the inflated profile of the balloon, impacts the crossing profile of over-the-wire angioplasty dilatation balloon catheters because the materials most suitable for use in the construction of the balloon components of angioplasty catheters are relatively non-compliant. Further progress in reducing the crossing profile of an over-the-wire system of the prior art is constrained by the need to maintain the inflated balloon profile of the device within the therapeutic range (i.e., 1.5-4.0 mm for coronary catheters and 4-10 mm for peripheral vascular catheters).

The second factor, the thickness of the walls of the balloon component, also impacts the crossing profile of over-the-wire devices of the prior art. The crossing profile of over-the-wire catheters has been reduced by decreasing the thickness of the walls of the balloon component. However, the wall thickness of the balloon component must remain within a range that confers satisfactory pressure tolerance and balloon durability.

The third factor influencing the crossing profile is the profile of the inner member of the balloon. The luminal profile of the inner member of the balloon component of prior art over-the-wire systems must exceed the maximal profile of the guidewire mandrel contained within the system to enable bidirectional separation of the catheter component from the guidewire component of these systems. Separability of the guidewire component form the catheter component constitutes one of the fundamental functional advantages of this class of catheters. This feature affords the opportunity to accomplish a catheter exchange without the need to sacrifice intraluminal access during this process. The factors that influence the profile of the balloon component inner member of prior art devices include: (a) the maximal profile of the guidewire mandrel contained within the device; (b) the magnitude of the catheter-guidewire clearance within the vicinity of the balloon component of the catheter; and (c) the thickness of the walls of the balloon component inner member. In some prior art catheters the maximal (i.e. proximal) profile of the guidewire mandrels contained within these devices has been reduced with the aim to reduce the crossing profile of the composite device. Unfortunately, this approach reduces both the "trackability" and the directional control or "steerability" of these systems. The trackability of a catheter is the facility with which a catheter can be advanced over a guidewire. It varies as a function of the rigidity of the guidewire contained within the system, which for prior art devices varies as a function of the profile of the guidewire mandrel. Reducing the profile of the guidewire mandrel compromises the rigidity of the guidewire and adversely affects the trackability of the composite system.

Reducing the proximal profile of the guidewire mandrel invariably compromises the directional control of the composite system because the steerability of a prior art over-the-wire system varies as a function of the profile of the proximal aspect of the guidewire mandrel contained within the system. Hence, further progress in reducing the profile of the balloon component inner member and ultimately the crossing profile of an over-the-wire dilatation balloon delivery system is constrained by the need to: maintain the proximal profile of the guidewire mandrel within a range that confers satisfactory trackability to the system, maintain the proximal profile of the guidewire mandrel within a range that confers satisfactory directional control to the system, and maintain the profile of the guidewire channel within the balloon component inner member sufficiently large to accommodate the proximal profile of said guidewire mandrel.

The magnitude of the catheter-guidewire clearance within the vicinity of the balloon also impacts the profile of the balloon component inner member and hence the crossing profile of the composite device. Reducing the magnitude of the catheter-guidewire clearance reduces the directional control of the device. The directional control of an over-the-wire system of the prior art varies directly as a function of the magnitude of rotational torque that can be delivered to the distal aspect of the guidewire. The efficiency with which this rotational torque can be transmitted within the confines of an over-the-wire system of the prior art varies, in part, with the magnitude of the catheter/guidewire clearance. Further progress in reducing the crossing profile of an over-the-wire device of the prior art is constrained by the need to maintain the magnitude of the catheter-guidewire clearance within a range that permits satisfactory guidewire-mediated torque delivery and hence satisfactory directional control.

The thickness of the walls of the balloon component inner member also impacts the profile of the inner member and hence the crossing profile of the composite device. The inner member confers column strength (i.e., resistance to coaxial compression) to the catheter. The magnitude of column strength conferred by the inner member varies directly with the thickness of the walls of the inner member (provided that comparable materials are used in the construction of the respective inner members). The column strength of a particular device profoundly influences the feasibility with which the device can be negotiated within the confines of critically stenotic lesions. Prior art catheters with thinner balloon component inner member walls, the catheters generally suffer from reduced pushability or column strength. Any further reduction in the crossing profile of conventional over-the-wire devices is constrained by the need to maintain the thickness of the walls of the inner member within a range that confers satisfactory column strength to the composite system.

In short, using prior art techniques there is a lower limit to the crossing profile that can be achieved in the construction of functionally suitable over-the-wire catheters, given the constraints inherent to the design of these systems and the limitations of current technology. This circumstance largely accounts for the fact that the majority of current generation over-the-wire catheters are similar in crossing profile.

Given the aforementioned limitations, a variety of more recent catheter configurations have been developed that enable the construction of guidewire-directed balloon delivery systems with lower crossing profiles. These more recently developed systems include: (1) "semi-movable" catheter systems, (2) "fixed-wire" catheter systems and (3) "balloon-on-a-wire" catheter systems. These devices are distinguished by virtue of the relative mobility of the guidewire components contained within these systems. "Semi-movable" catheters permit full rotational and limited coaxial mobility of the guidewire components relative to the catheter components of these systems. U.S. Pat. No. 4,616,653 describes a semi-movable system. "Fixed-wire" catheter systems permit variable rotational mobility of the guidewire components relative to the catheter components of these systems and yet they afford no coaxial catheter-guidewire mobility. U.S. Pat. No. 4,582,181 describes a fixed-wire system. "Balloon-on-a-wire" devices do not provide any mobility of the guidewire components relative to the balloon components of these systems. Directional control of these devices is accomplished by rotating the entire device. International Patent Application No. PCT/US86/00983 describes a balloon-on-a-wire device.

Each of these systems are easier to prepare, and more convenient to use relative to over-the-wire systems because they contain pre-installed guidewires. Each of these devices can be advanced within the confines of critical lesions with greater facility relative to over-the-wire devices of the prior art because they have lower crossing profiles.

The structural advantages of non-over-the-wire devices largely have been achieved at the expense of functional trade-offs. None of these systems permit separation of the guidewire components from the respective catheter components. Hence, their use obligates sacrificing intravascular access in the event that a catheter exchange is required. This circumstance, in turn, mandates the renegotiation of a lesion with a second guidewire during the course of a catheter exchange, a process that contributes to the duration, complexity and morbidity of the procedure.

Selected fixed-wire and all balloon-on-a-wire systems of the prior art also afford compromised guidewire mobility and hence, directional control and reach and ccross potential relative to over-the-wire and semi-movable systems. This disadvantage arises because the majority of these devices contain bonds between the balloon and guidewire components of these systems. U.S. Pat. No. 4,582,181 describes a fixed-wire device that contains a bond between the balloon and guidewire components of the device. International Patent Application No. PCT/US86/00983 describes a balloon-on-a-wire device that similarly contains a bond between the balloon component and guidewire component of the system.

The inability to advance and withdraw the guidewire component independently of the balloon component of these systems further complicates the process of performing intraoperative angiography. Typically, the balloon component of a catheter/guidewire system must be withdrawn completely from the vasculature to enable the performance of intraoperative angiography with satisfactory resolution. Intraoperative angiography is commonly performed following balloon dilatation, during the course of an angioplasty procedure, to assess the impact of the procedure on the configuration of the lesion requiring dilatation.

Semi-movable and over-the-wire devices readily permit intraoperative angiography. The catheter components of these systems can be withdrawn over the respective guidewire components, to enable the performance of intraoperative angiography, without sacrificing intraluminal guidewire access during this process. In the event that additional dilatation is required following angiography, the balloon components of these systems can be readvanced over the respective guidewire components across the confines of the respective stenoses and re-inflated. Because fixed-wire and balloon-on-a-wire systems of the prior art do not afford coaxial guidewire mobility, the use of these devices obligates sacrificing intraluminal access during the performance of intraoperative angiography. Hence, their use exposes the patient to the added risk associated with renegotiation of the lesion, when subsequent dilatation is required.

In summary, there currently exist a variety of functional and structural trade-offs intrinsic to the designs of prior art dilatation balloon catheter systems. Over-the-wire systems afford safety and directional control at the expense of crossing profile. Semi-movable systems of the prior art afford directional control and modest advantages in terms of crossing profile at the expense of procedural safety. Selected fixed-wire and balloon-on-a-wire systems afford significant advantages in terms of crossing profile at the expense of procedural safety and directional control. Clearly, there exists a need for a catheter configuration that enables the construction of a guidewire-directed dilatation balloon delivery system that offers: (1) the crossing profile of a balloon-on-a-wire or fixed-wire device, (2) the coaxial/rotational guidewire mobility (i.e. steerability), and convenience of a semi-movable device, and (3) the procedural safety of an over-the-wire device.

SUMMARY OF THE INVENTION

The angioplasty balloon dilatation catheter of our invention provides numerous advantages relative to the prior art. The invention permits the construction of a highly steerable and entirely separable guidewire-directed dilatation balloon catheter system with a lower crossing profile relative to prior art over-the-wire catheters of commensurate inflated balloon size that accommodate guidewires of commensurate proximal profile. In fact, our invention permits the construction of a device with a crossing profile that is comparable to state-of-the-art fixed-wire and balloon-on-a-wire devices of commensurate inflated balloon size. This is accomplished by: (1) constructing the balloon component inner member with a particularly low profile, and (2) disposing the balloon component inner member over a relatively low profile segment of a guidewire of non-uniform profile. The luminal dimensions of the balloon component inner member of the catheter component of our system is less than the profile of the proximal and distal aspects of the guidewire contained within the system. The lower crossing profile of our device enables it to be introduced across the confines of critical stenoses with less force and with less potential for catheter induced trauma relative to prior art over-the-wire systems of commensurate inflated balloon size that accommodate guidewires of commensurate proximal profile.

Additionally, the invention permits the construction of a low profile guidewire-directed dilatation balloon catheter that affords excellent directional control. This is accomplished by disposing within the device a guidewire containing a tapered mandrel of relatively large proximal profile. Our invention provides unimpaired rotational and limited unimpaired coaxial guidewire mobility. The extent to which the guidewire can be advanced and/or retracted freely within the confines of the catheter is a function of the configuration of the guidewire. Specifically, the extent to which the guidewire can be advanced and retracted is determined by the length of the guidewire segment contained by the balloon component inner member, which segment is lower in profile than the luminal dimensions of the balloon component inner member. Advancing or retracting the guidewire beyond this region brings the opposing surfaces of the guidewire and catheter into direct contact, and thereby partially impairs the relative mobility of these two system components. The ability to advance and retract the guidewire component relative to the catheter component enhances the reach and cross potential of the device and facilitates the performance of intraoperative angiography.

The catheter/guidewire system of our invention permits complete separation of the catheter component from the guidewire component of the system. This is accomplished by constructing the balloon component inner member of the device in a manner that enables it to expand or unfold radially and thus accommodate the changes in profile of the guidewire as the guidewire is advanced or withdrawn therethrough. The inner member is designed to accommodate these changes in profile with relative ease. The catheter component of the system of our design can be withdrawn over the guidewire component and completely separated therefrom, enabling the performance of a catheter exchange without sacrificing intraluminal access. Similarly, the guidewire component can be withdrawn through the confines of the catheter component and readvanced therethrough, enabling the performance of a guidewire exchange without removing the catheter from the vasculature.

The use of a radially expandable inner member in combination with a guidewire of non-uniform profile enables the construction of an ultra-low profile, highly steerable, entirely separable, guidewire-directed dilatation balloon catheter system that is lower in crossing profile and more convenient to use than over-the-wire catheters of the prior art. In addition, our catheter is safer to use compared to semi-movable systems of the prior art and safer to use and easier to direct compared to fixed-wire and balloon-on-a-wire systems of the prior art. These features enable the catheter of our invention to be used in the performance of an angioplasty procedure with less effort and with greater finesse than both over-the-wire and non-over-the-wire systems of the prior art.

The foregoing and other aspects of the invention will become apparent from the following detailed description, illustrations and claims.

BRIEF DESCRIPTION OF THE DRAWINGS

FIGS. 11G and 11H are enlarged cross-sectional views of the mid/distal-shaft.

DESCRIPTION OF THE PREFERRED EMBODIMENTS

FIG. 1 is a series of views of a preferred embodiment of our catheter/guidewire system. FIGS. 1B, 1F and 1G are side (or profile) views, while FIGS. 1A, 1C, 1D and 1E are cross-sectional views at different positions along the length of the catheter/guidewire assembly.

The system consists of a catheter component and a guidewire component. The catheter component consists of everything in FIG. 1A except the guidewire 90. The guidewire 90 is semi-permanently contained within the catheter, as will be explained further below. The catheter consists of a balloon component 50, a multi-channel catheter shaft (see FIG. 1A), and a proximal adapter 100. The balloon component is formed of a high strength polymeric material, for example, polyethylene terephthalate, commonly known as PET. The use of this material enables the construction of a high pressure-tolerant balloon that contains particularly thin walls.

Figure 1A:
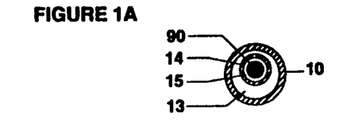
FIGS. 1A to 1G are views of a preferred embodiment of our catheter/guidewire system.

The shaft consists of an outer member 10 and an inner member 14 that are disposed coaxially with respect to one another. The catheter thus contains two separate lumens, a guidewire lumen 15 that extends continuously throughout the catheter and an hydraulic lumen 13 that is continuous with the confines of balloon 50 to enable the balloon to be inflated.

Figure 1B:
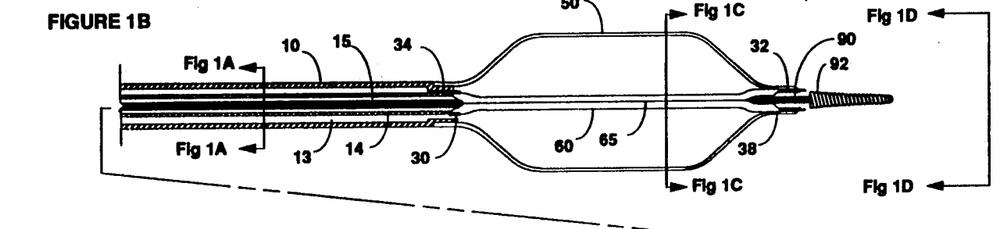
Figure 1C:
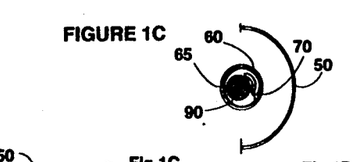
Figure 1D:
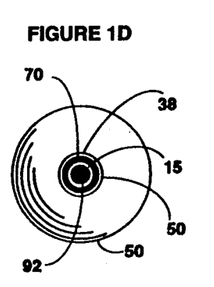
Figures 1E, 1F:
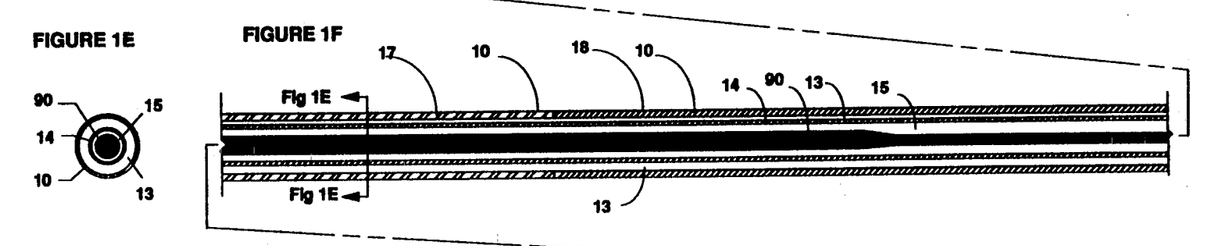
Figure 1G:
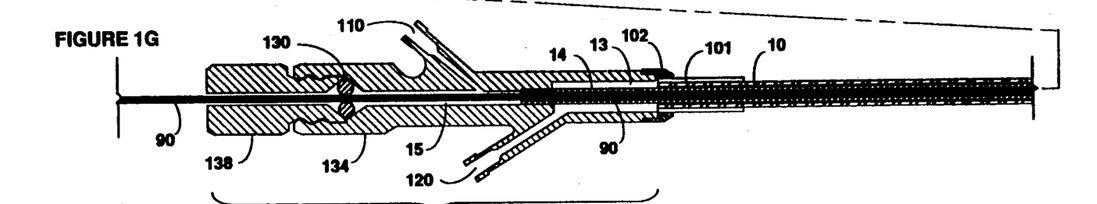

The outer member 10 of the shaft is preferably composed of two or more tubular components joined together end to end (see FIG. 1F). The proximal component 17 is more rigid than the distal component 18. In one system component 17 is polyimide while component 18 is a polyimide/polyurethane blend. These components are joined by means of well known hydraulically competent bonds. The use of two or more components for the shaft improves pushability and trackability relative to conventional catheters which have catheter shafts of uniform rigidity throughout.

The inner tubular member includes a proximal tubular member and a multi-layered segment 60, 70 that extends throughout the confines of the balloon. The multi-layered segment consists of a very flexible and particularly thin-walled tubular member 70 (see FIG. 1C) and a relatively more rigid tubular member 60 (see FIG. 1B). This flexible member 70 is considerably larger in luminal profile than the corresponding profile of the guidewire contained therein at the onset of a procedure and, as a result, is folded or wrapped around the wire. A relatively more rigid tubular member 60 holds the flexible member folded in place around the guidewire. In FIG. 1B the more rigid member 60 is wrapped around member 70 preventing it from showing in that figure. (FIG. 1B is a profile view taken off-center from the axis of the system.) The flexible tubular member 70 provides hydraulic competence to the balloon component inner member by preventing fluid used to inflate the balloon from escaping along the guidewire. The relatively more rigid tubular member 60 provides column strength to the balloon component inner member.

Importantly, the profile of tubular member 60, within the mid-span of the balloon, is considerably less than the unfolded profile of tubular member 70. The profile of the unfolded tubular member 70 is sufficient to accommodate the largest profile segment of the guidewire contained by the device. Tubular members 60 and 70 are joined proximally and distally and they are movable therebetween. The proximal end of tubular member 70 is bonded to the shaft outer member 10 at joint 34 and the distal end is bonded to the balloon 50 at joint 38. The proximal bond 34 maintains the coaxial relationship between the distal ends of the inner and outer components of the catheter shaft and thus precludes the development of tension/compression distortion of the relatively delicate balloon inner member suspended therebetween. The distal bond 38 completes the hydraulic competence of lumen 13.

Because tubular member 70 is confined within a space defined by the external surface of guidewire 90 and the luminal surface of tubular member 60, it is not subject to considerable stress during balloon inflation. Furthermore, because tubular member 70 is not required to provide column strength to the balloon, tubular member 70 can be constructed with particularly thin walls. This enables the walls of tubular member 70 to be folded over one another within the confines of member 60 without significantly affecting the crossing profile of the composite structure. Member 60 contains one or more slits 65 that extend longitudinally along its full length, thereby enabling it to expand radially as tubular member 70 unfolds to accommodate changes in the guidewire profile during movement of the catheter or guidewire.

Figure 2A:
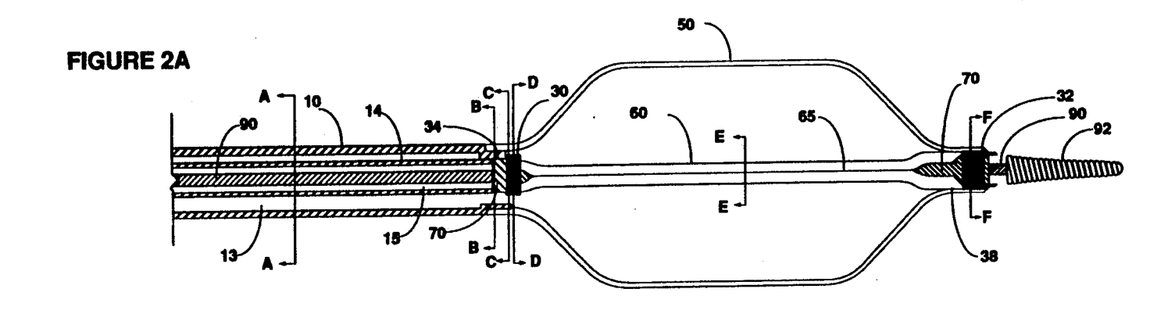
FIGS. 2A–2H are profile views and cross-sectional views of the distal aspect of the preferred embodiment of the catheter/guidewire system.
Figures 2B, 2C, 2D, 2E, 2F, 2G:
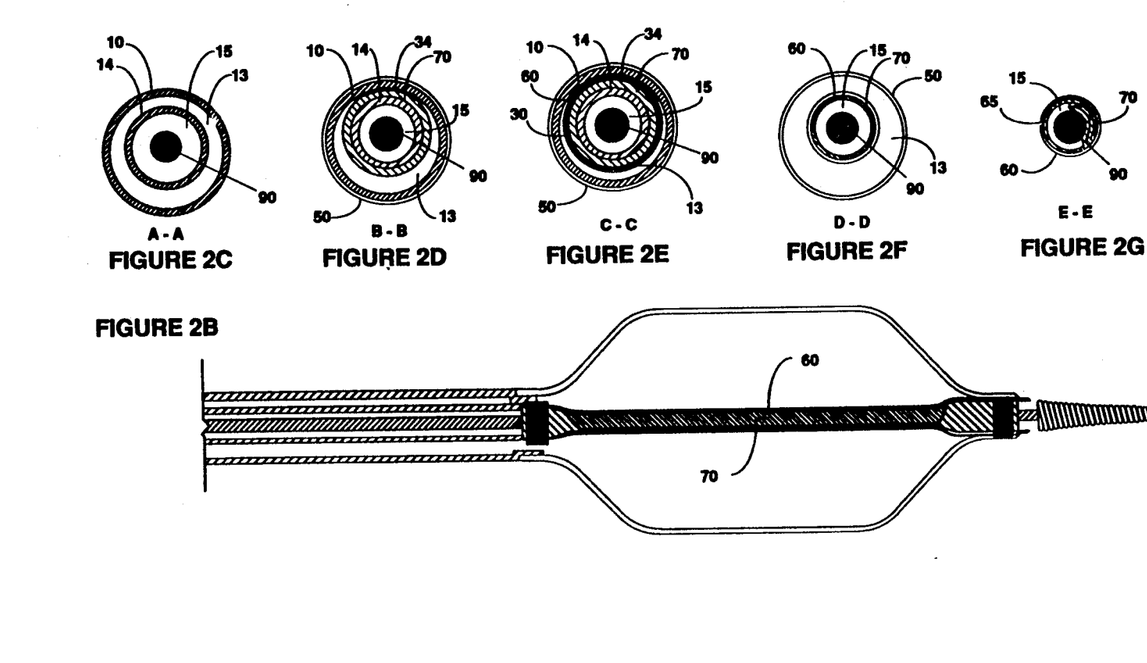
Figure 2H:
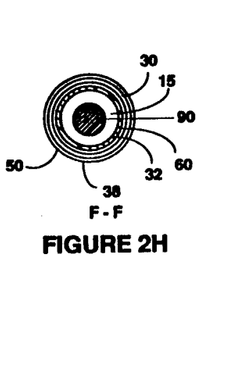

Preferably, tubular member 70 is folded longitudinally within the confines of tubular member 60 such that the fold in tubular member 70 is contralateral to the slit in member 60 (see FIG. 2G). This configuration minimizes the possibility of the guidewire 90 escaping the confines of member 60. The aforementioned configuration permits the construction of a particularly low profile, hydraulically competent inner member that is capable of radial expansion in response to the application of minimal radially directed force.

The distal portion of the catheter system contains proximal and distal radiopaque marker bands 30, 32 that function to identify the location of the balloon during fluoroscopic evaluation. The distal radiopaque marker band 32 and the radiopaque guidewire coil 92 also fluoroscopically identify the distal tip of the catheter and guidewire components of the system respectively. The ability to determine the spatial relationship between the catheter and guidewire components, under fluoroscopic viewing, enables the operator to advance and retract the guidewire relative to the catheter without inadvertently withdrawing the guidewire coil within the confines of the balloon.

The proximal adapter 100 (see FIG. 1G) contains two side ports 110 and 120 which interface with male luer-locking components. Sideport 110 provides access to the catheter guidewire lumen 15 and sideport 120 provides access to the catheter hydraulic lumen 13. The infusion of fluid into sideport 120 inflates the balloon 50. A deformable sealing O-ring 130 is contained between two rotatably disposed elements 134 and 138. The interface between elements 134 and 138 is a right-hand screw. Clockwise rotation of element 138 relative to element 134 compresses the flexible O-ring 130 between the opposing surfaces of the proximal adapter 100 and the guidewire 90, thus creating a hydraulically competent seal at the proximal end of the guidewire lumen 15. This seal precludes inadvertent loss of blood via the guidewire lumen 15 during the course of an angioplasty procedure. The action of this seal tends to seize the guidewire 90 to the catheter and, when closed, restricts coaxial mobility of the guidewire relative to the catheter. Counter-clockwise rotation of element 138 relative to element 134 releases the guidewire from the catheter, enabling the operator to freely advance, retract and rotate the guidewire relative to the catheter and thereby direct the system within the confines of the vasculature. It is anticipated that an operator will advance the device within the confines of the vasculature with the seal open, close this seal following manipulation of the device across the confines of the lesion requiring dilatation, and then perform the dilatation. Closure of this seal does not preclude rotation of the guidewire within the confines of the device. Hence, it is anticipated that the operator might elect to advance the device, with the seal closed, provided coaxial mobility is not required. A strain relief interface 101 is attached to the catheter shaft outer member 10 and to the distal end of the proximal adapter 100 by means of a cap 102.

As shown in FIG. 1, in the preferred embodiment the guidewire 90 is non-uniform in profile. Preferably, the guidewire contains at least one low profile segment that is disposed, at least at the outset of the angioplasty procedure, within the confines of the balloon, as has been described above.

The guidewire 90 consists of a tapered mandrel, a flat wire ribbon (not shown) and a radiopaque guidewire coil 92. The guidewire coil extends over the distal aspect of the mandrel obscuring the ribbon in the drawings. The flat wire ribbon extends throughout the length of the interior of the guidewire coil 92. The guidewire coil 92 is joined proximally to the guidewire mandrel and to the flat wire ribbon. Distally, the guidewire coil is joined only to the flat wire ribbon. The profile of the coil is non-uniform. (See FIG. 1.) This configuration confers a wedge function to the guidewire.

In the preferred embodiment, the distal thirty centimeters of the guidewire mandrel is smaller in profile than the luminal dimensions of the non-expanded balloon component inner member. This configuration enables unimpaired coaxial guidewire movement within the confines of the balloon component inner member for a distance of 27 centimeters. (The coil occupies about 3 centimeters.) This feature enhances the reach and cross potential of the device and enables the performance of intraoperative angiography with enhanced efficiency and safety relative to devices that do not provide coaxial catheter/guidewire movement. The proximal end of the guidewire contains an adapter (not shown) that interfaces with an extension wire.

FIGS. 2A and 2B are enlarged profile views of the distal aspect of the preferred embodiment of the catheter/guidewire system. In FIG. 2B member 60 has been partially removed to illustrate folded tubular member 70 contained therein. FIGS. 2C–2H illustrate enlarged cross-sectional views of the structure of FIG. 2A.

Figure 3A:
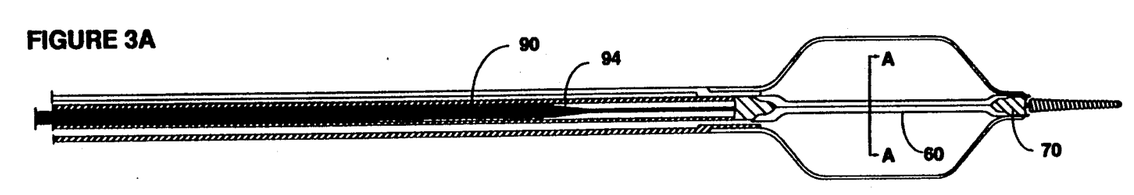
FIG. 3A is a profile view of a preferred embodiment of the catheter/guidewire system, and enlarged
Figure 3B:
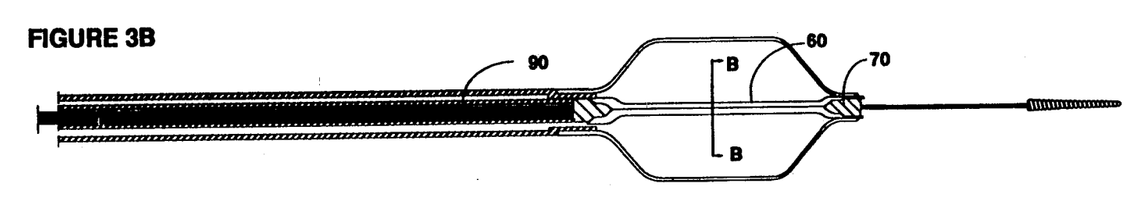
FIG. 3B illustrates the unimpaired coaxial catheter-guidewire mobility of the preferred embodiment.
Figure 3C:
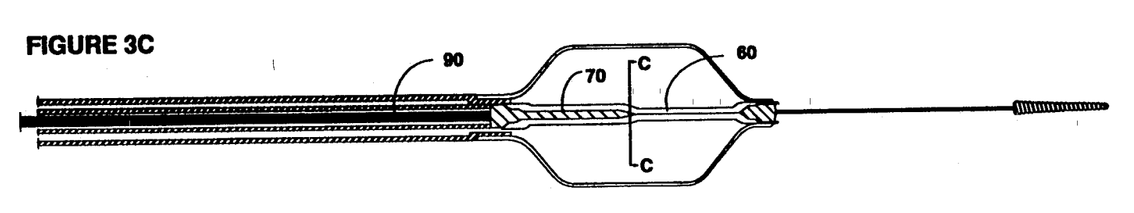
FIGS. 3C–3D illustrate the change in configuration that transpires within the balloon component inner member with the withdrawal of the catheter component over a taper in the guidewire mandrel.
Figure 3D:
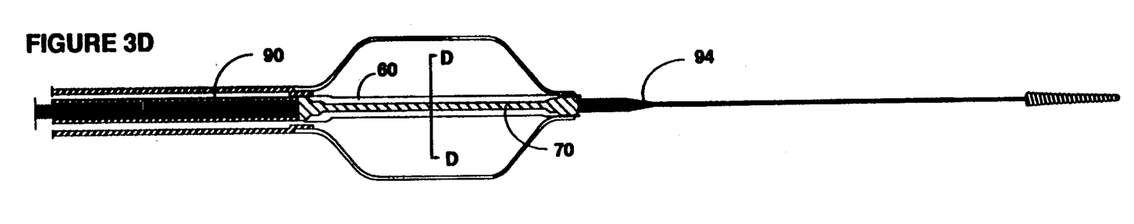
Figure 3E:
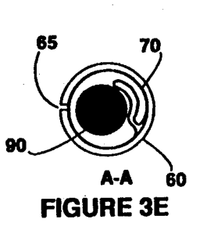
FIG. 3E is a corresponding enlarged cross-sectional view of the balloon component inner member.
Figure 3F:
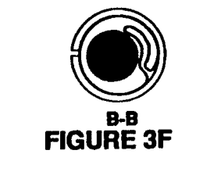
FIG. 3F is a corresponding enlarged cross-sectional view.
Figure 3G:
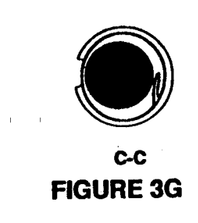
FIG. 3G and 3H are corresponding enlarged cross-sectional views of FIGS. 3C and 3D.
Figure 3H:
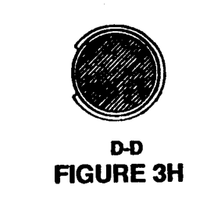
Figure 4A:
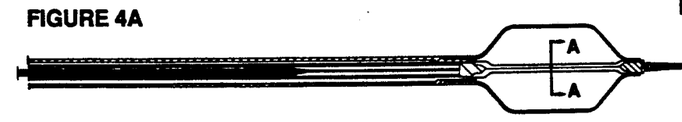
FIGS. 4A–4G are a series of profile views of the distal aspect of the preferred embodiment of the catheter/guidewire system.
Figure 4B:
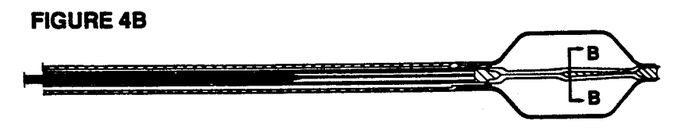
Figure 4C:
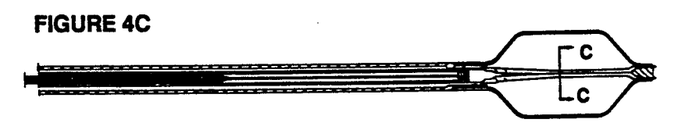
Figure 4D:
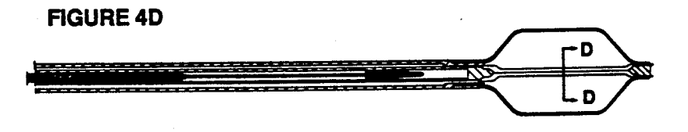
Figure 4E:
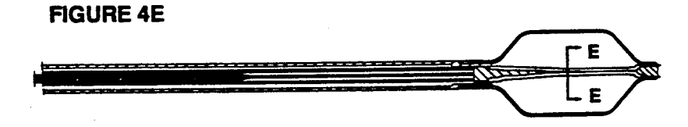
Figures 4F, 4M:
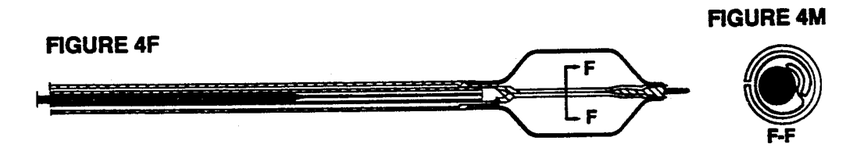
FIGS. 4H to 4N illustrate enlarged cross-sectional views of the balloon component inner member.
Figures 4G, 4N:
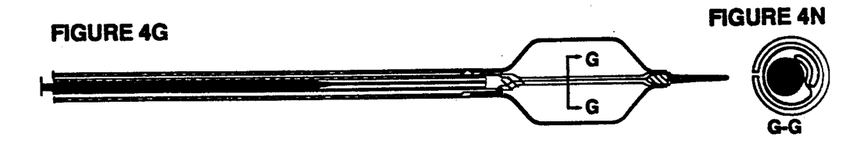
Figure 4H:
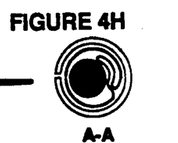
Figure 4I:
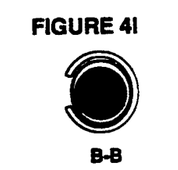
Figure 4J:
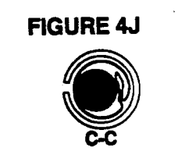
Figure 4K:
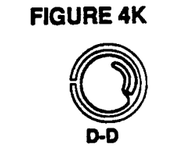
Figure 4L:
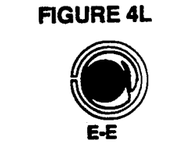

FIGS. 3A–3H illustrate the change in configuration of the balloon component inner member that transpires as the catheter is withdrawn over a taper 94 in the guidewire 90. As illustrated in FIG. 3B, the catheter component can be withdrawn for a limited distance (e.g., approximately 27 centimeters in the preferred embodiment) over the guidewire without distorting the configuration of the inner member 60, 70. This occurs because the profile of the segment of the guidewire mandrel in the vicinity of the balloon is less than the non-radially expanded luminal dimensions of the inner member of the balloon. The process of advancing and retracting the relatively larger profile elements of the guidewire through the confines of the balloon provokes modest resistance. This resistance develops in response to the force required to radially expand the inner member within the confines of the balloon. The magnitude of force required to radially expand the inner member 60, 70 of our device is well within an acceptable range for the performance of an angioplasty procedure. As illustrated in FIGS. 3C–3D, and corresponding enlarged cross-sections FIGS. 3G–3H, the tapers in the guidewire radially expand the relatively rigid member 60 and unfold the relatively more flexible tubular member 70.

FIGS. 4A–4G, and corresponding enlarged cross-sectional views FIGS. 4H to 4N, illustrate the change in configuration that transpires within the balloon component inner members 60, 70 during withdrawal and readvancement of a non-uniform guidewire component therethrough. In the preferred embodiment, the catheter of our device can be completely separated from the guidewire by withdrawing the catheter from the guidewire or vice versa. Similarly, a guidewire of either our design or conventional configuration can be advanced through the confines of the catheter component of our device.

Figure 5A:
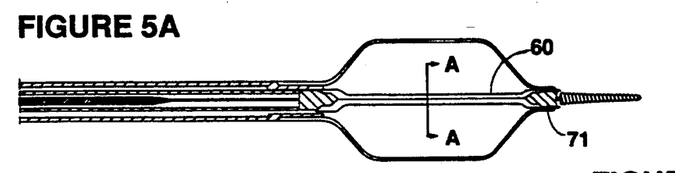
FIG. 5A is a profile view of the distal aspect of another embodiment of a catheter/guidewire system illustrating an elastomeric tubular balloon component inner member.
Figure 5B:
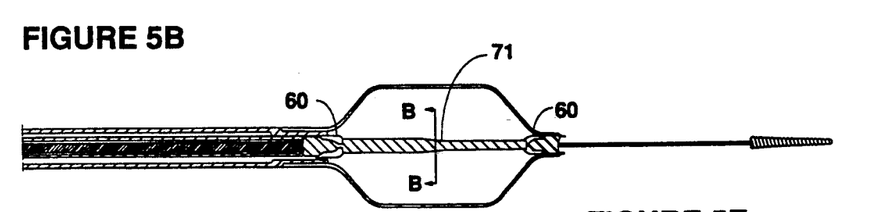
FIG. 5B-5C illustrate the change in configuration that transpires within the elastomeric tubular component as the catheter is withdrawn over a taper in the guidewire, and as the guidewire is withdrawn from the catheter.
Figure 5C:
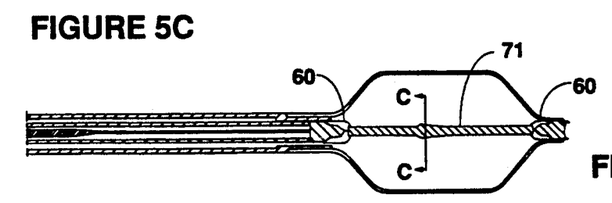
Figure 5D:
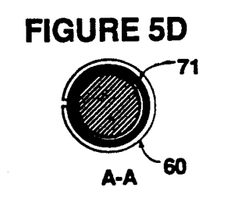
FIG. 5D is an enlarged cross-sectional view of the inner member.
Figure 5E:
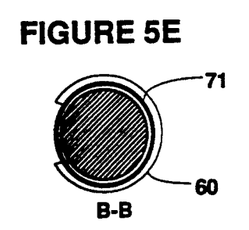
FIGS. 5E and 5F are corresponding enlarged cross-sectional views.
Figure 5F:
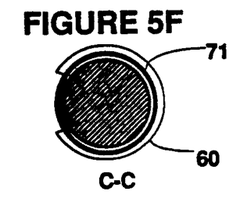

FIGS. 5A–5C illustrate another embodiment of a catheter/guidewire system that contains a radially expandable inner member and a guidewire of non-uniform profile. The inner member of this embodiment contains an elastomeric inner tubular member. FIGS. 5A–5C illustrate the change in configuration that transpires within the elastomeric tubular member 71 of this embodiment as a non-uniform profile guidewire is advanced and withdrawn therethrough. In this embodiment, member 60 confers column strength and elastomeric member 71 confers hydraulic competence to the balloon component inner member. For the purpose of clarity, the majority of tubular member 60 has been removed in FIGS. 5B–5C. The respective enlarged cross-section FIGS. 5D to 5F illustrate the change in thickness that occurs within elastomeric tubular member 71 as it expands and contracts to accommodate changes in the guidewire profile.

Figure 6A:
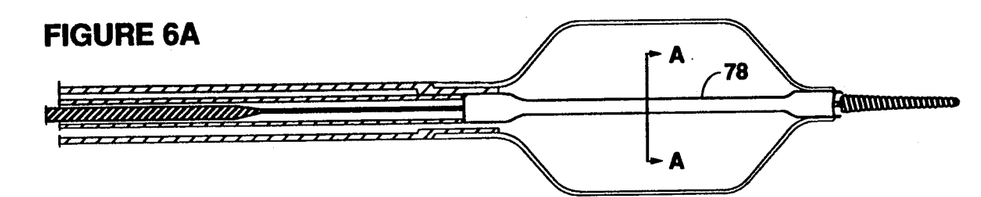
FIG. 6A is a profile view of the distal aspect of another embodiment of a catheter/guidewire system that contains an elastomeric tubular member disposed outside another tubular member.
Figure 6B:
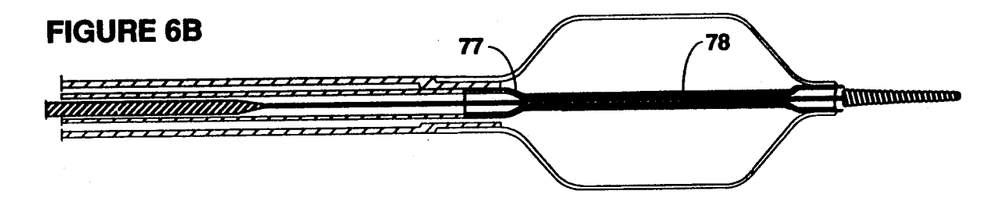
FIG. 6B is a full profile view of the balloon component inner member.
Figures 6C, 6D, 6F:
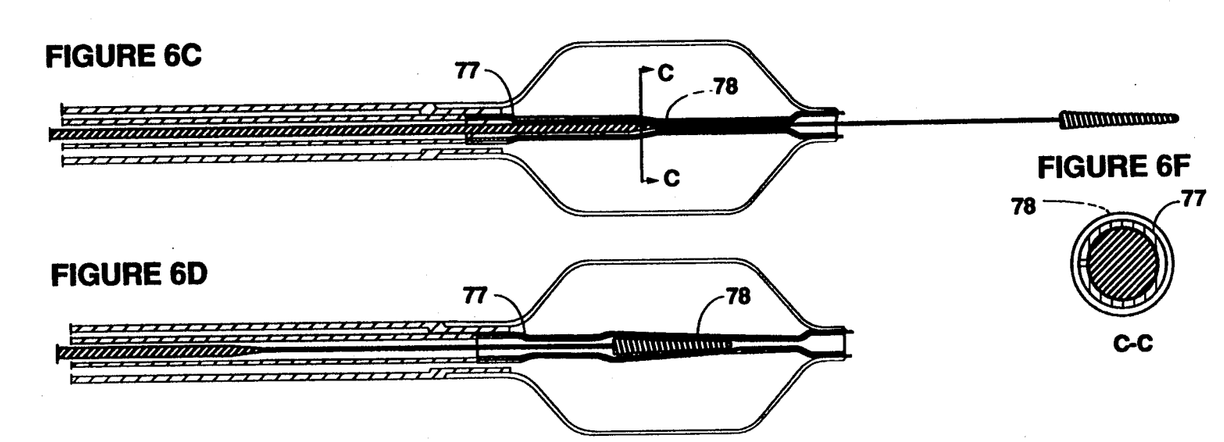
FIGS. 6C-6D illustrate the change in configuration that transpires within an elastomeric tubular member as the catheter is withdrawn over a taper in the guidewire, or the guidewire is withdrawn from the catheter component.
FIG. 6F is an enlarged cross-sectional view of said inner member.
Figure 6E:
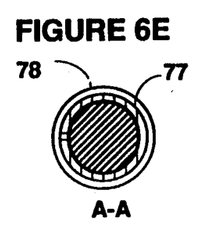
FIG. 6E is an enlarged cross-sectional view.

FIGS. 6A–6D illustrate another embodiment of a catheter/guidewire system that contains a radially expandable inner member and a guidewire of non-uniform profile. The inner member of this embodiment contains a relatively rigid tubular member 77 that is disposed within an elastomeric tubular member 78. FIG. 6A is a profile view of the catheter/guidewire system. FIG. 6B contains a profile view of same, but also shows an internal view of region 78. In this embodiment, tubular member 77 confers column strength, while elastomeric member 78 confers hydraulic competence to the balloon component inner member. FIGS. 6C and 6D illustrate the change in configuration that transpires within the inner member of this embodiment as the guidewire is advanced and withdrawn relative to the catheter. FIGS. 6E and 6F depict enlarged cross-sections of FIGS. 6A and 6C, respectively.

Figures 7A, 7D:
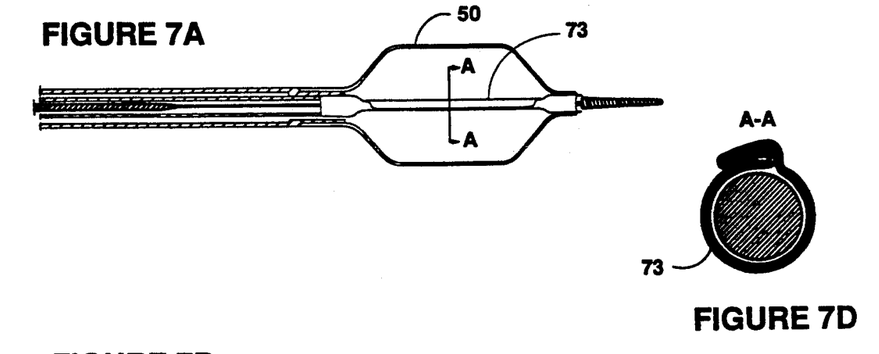
FIG. 7A is a profile view of the distal aspect of another embodiment of a catheter/guidewire system that contains a wrapped balloon component inner member.
FIG. 7D is an enlarged cross-sectional view of the balloon component inner member.
Figure 7B:
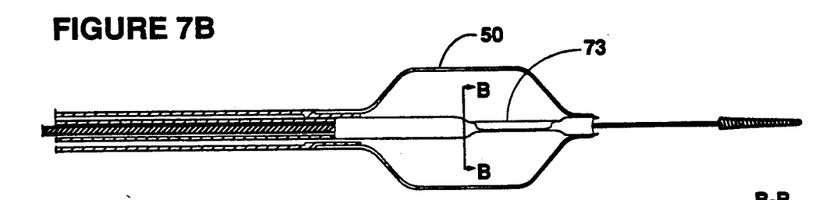
FIGS. 7B-7C illustrate the change in configuration that transpires within the wrapped balloon component inner member as the catheter is withdrawn over a taper in the guidewire, or the guidewire is withdrawn from the catheter.
Figure 7C:
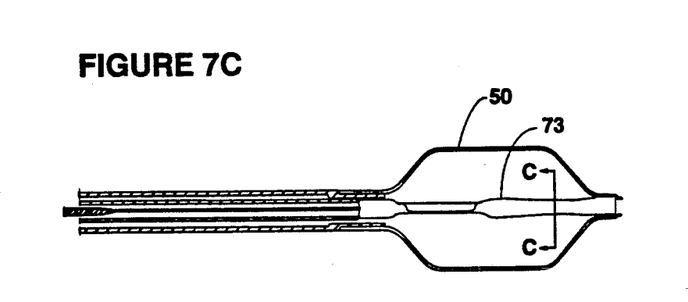
Figure 7E:
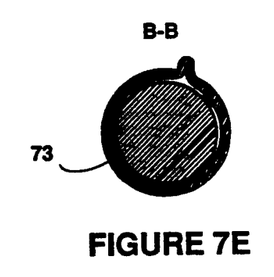
FIGS. 7E and 7F are enlarged cross-sectional views of the balloon component inner member.
Figure 7F:
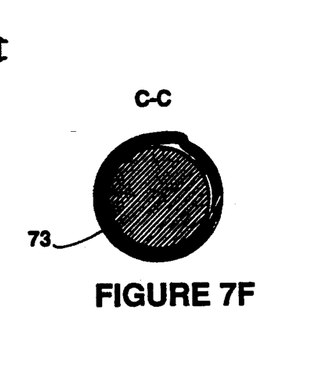

FIGS. 7A–7C illustrate another embodiment of a catheter/guidewire system of our invention. This embodiment contains a folded, or wrapped, relatively inelastic and yet radially expandable single component inner member 73 that extends within the balloon 50. In this embodiment, the inner member is composed of a tubular member of uniform wall thickness. FIGS. 7B and 7C illustrate the change in configuration that transpires within the single component inner member 73 of this embodiment consequent with the process of advancing or retracting a guidewire of non-uniform profile therethrough. Reversible bonding, for example by heat, ultrasound or adhesive, or molding, for example by heat, can be used to maintain the desired wrapped or folded configuration. FIGS. 7D–7F are corresponding enlarged cross-sectional views.

Figure 8A:
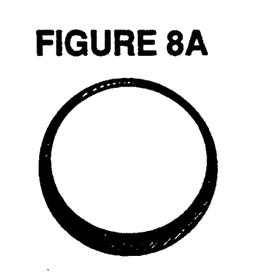
FIGS. 8A-8B illustrate unfolded and folded cross-sectional views of another embodiment of a radially expandable balloon component inner member composed of a tubular member of non-uniform wall thickness.
Figure 8B:
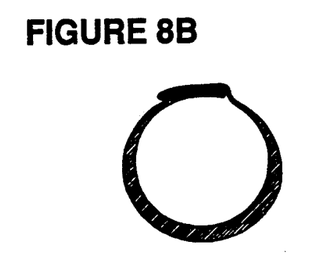

FIGS. 8A–8B illustrate cross-sectional views of another embodiment of a radially expandable inner member of a catheter/guidewire system. This embodiment consists of a folded or wrapped balloon having an inner member that is composed of a tubular member of non-uniform wall thickness. The non-uniform wall thickness enables the construction of an inner member that is more uniform in profile, when folded or wrapped, than does to the use of a tube of relatively uniform wall thickness. (See FIG. 8B). This configuration permits radial expansion, and if necessary reversible bonding or molding can be used to maintain the desired wrapped or folded configuration.

Figure 9A:
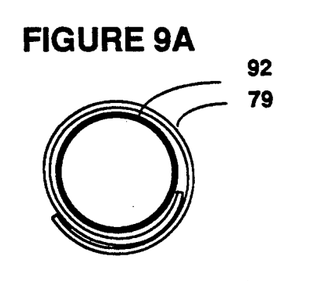
FIGS. 9A-9B are cross-sectional views of other embodiments of a radially expandable inner member that consists of a relatively rigid tubular member with overlapping surfaces that is disposed either outside or inside an elastomeric tubular member.
Figure 9B:
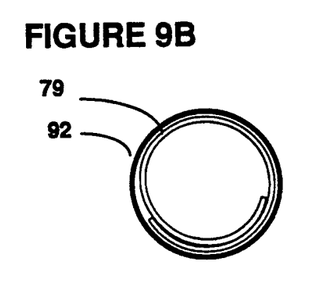

FIGS. 9A–9B illustrate cross-sectional views of another embodiment of a radially expandable inner member of a catheter/guidewire system. This embodiment consists of a relatively rigid tubular member 79 that is disposed either outside (see FIG. 9A) or inside (see FIG. 9B) of an elastomeric tubular member 92. Tubular member 79 is a relatively rigid tubular structure with overlapping surfaces. Tubular member 79 confers column strength to the inner member, while elastomeric tubular member 92 provides hydraulic competence.

Figure 10A:
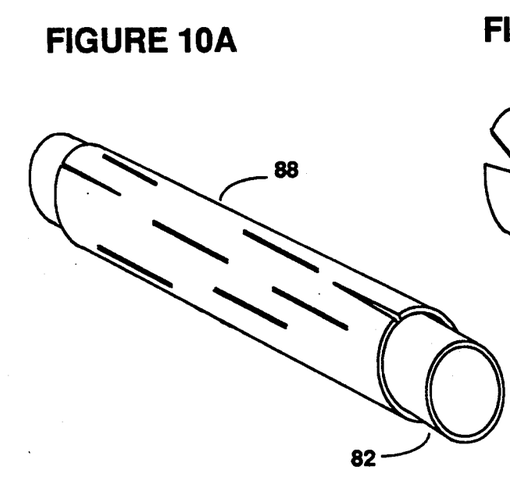
FIG. 10A is a perspective view of another embodiment of a radially expandable inner member that includes a relatively rigid tubular member 88 disposed either inside or outside of an elastomeric tubular member.
Figure 10B:
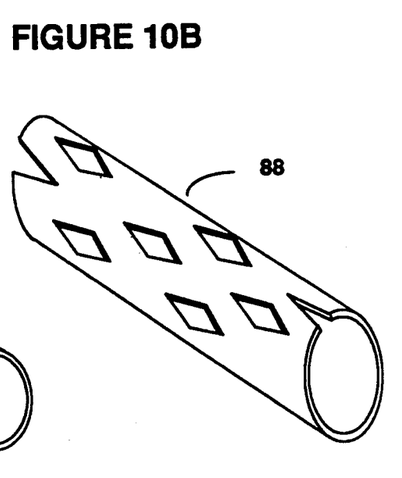
FIG. 10B illustrates the means by which the tubular member accommodates radial expansion.

FIGS. 10A–10B illustrate three-dimensional views of another embodiment of a radially expandable inner member of a catheter/guidewire system of our design. This embodiment contains a relatively rigid, tubular member 88 that is disposed either over (see FIG. 10A) or under a more flexible or elastomeric tubular member 82. Tubular member 88 provides column strength, while elastomeric tubular member 82 confers hydraulic competence to this embodiment. FIG. 10B illustrates the change in configuration of member 88 that transpires as it expands radially.

Figure 11A:
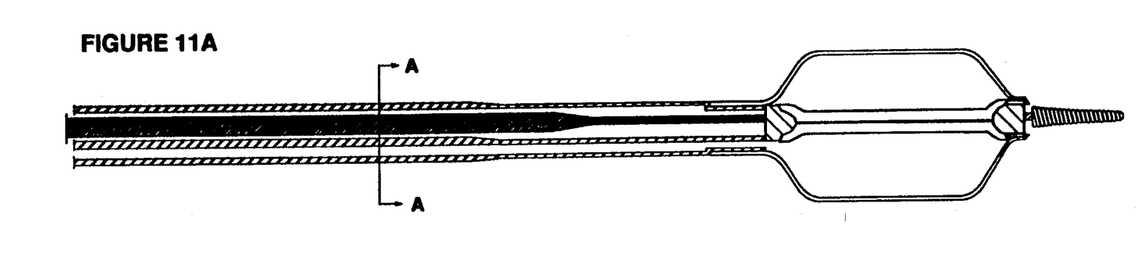
FIG. 11A is a profile view of another embodiment of a catheter/guidewire system that contains a radially expandable balloon component inner member and a non-coaxial multi-lumen catheter shaft.

FIG. 11A illustrates another embodiment of a guidewire-directed dilatation balloon catheter that contains a non-coaxial multi-lumen catheter shaft. This figure illustrates that our invention is not limited to the construction of catheters of coaxial shaft construction. Although the device depicted in FIG. 11A contains the preferred configuration for the balloon component inner member of our design, it should be recognized that any inner member, for example, as described above, that confers suitable column strength and permits radial expansion can be used in conjunction with a multi-lumen catheter shaft and guidewire of non-uniform profile. This configuration creates a completely separable, highly steerable guidewire-directed dilatation balloon catheter system of lower profile than heretofore possible.

Figure 11B:
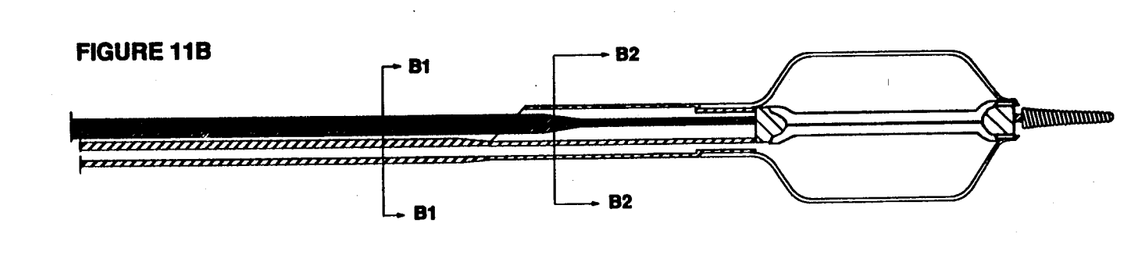
FIG. 11B is a profile view of another embodiment of a catheter/guidewire system that contains a radially expandable balloon component inner member and a non-coaxial multi-lumen catheter shaft.

FIG. 11B illustrates another embodiment of a guidewire-directed dilatation balloon catheter that is similar to the catheter configuration illustrated in FIG. 11A. However, the guidewire component 90 contained with the device, depicted in FIG. 11B, exits the confines of the catheter within the mid/distal-shaft of the device. This configuration enables the construction of an ultra-low profile guidewire-directed dilatation balloon catheter delivery system that affords the performance of a catheter exchange with enhanced facility and efficiency relative to prior art over-the-wire devices of conventional design.

Figure 11C:
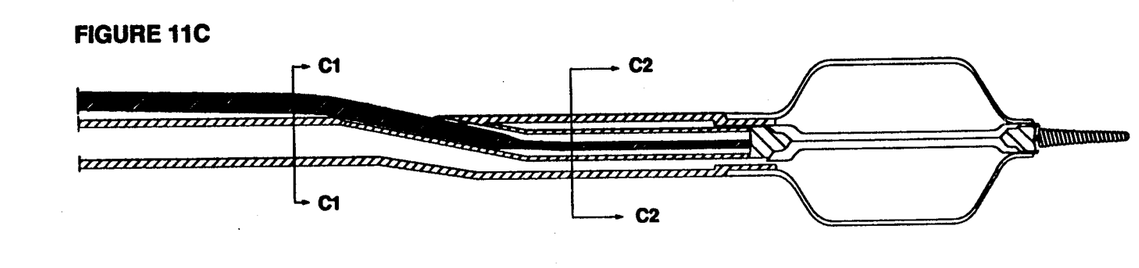
FIG. 11C is a profile view of another embodiment of a catheter/guidewire system.
Figure 11D:
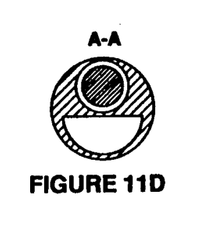
FIG. 11D is an enlarged cross-sectional view of the shaft.
Figure 11E:
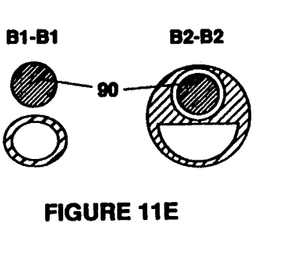
FIGS. 11E and 11F are enlarged cross-sectional views of the mid/distal-shaft.
Figure 11F:
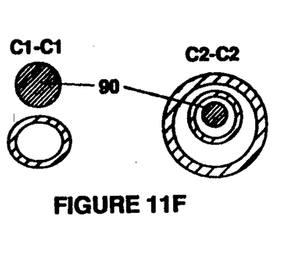

FIG. 11C illustrates another embodiment of a guidewire-directed dilatation balloon catheter system that is similar, in many respects to the device depicted in FIG. 11B. This embodiment differs from the previous one by virtue of the configuration of the catheter shaft. The region of the catheter shaft, containing the guidewire component, is largely coaxial.

As has been described, our invention enables the construction of an ultra-low profile, highly steerable guidewire-directed dilatation balloon catheter system that accommodates a guidewire of larger proximal and distal proportions relative to the luminal dimensions of all or a portion of the inner member. The catheter/guidewire system of our invention permits: (1) unrestricted rotation of the guidewire, (2) unimpaired limited coaxial guidewire mobility, (3) and complete catheter-guidewire separability. Our invention enables the construction of a guidewire-directed dilatation balloon catheter system with a substantially lower crossing profile and yet commensurate steerability and safety relative to over-the-wire systems of the prior art. Our invention further enables the construction of a catheter/guidewire system that affords the convenience of a fixed-wire or semi-movable device. The guidewire contained within our device is non-uniform in profile. All or a segment of the inner member of our device unfolds or expands radially to accommodate changes in the guidewire profile with minimal resistance.

The use of our invention enables the performance of an angioplasty procedure with less effort and greater finesse than prior art devices. In addition, the use of our invention enables the performance of an intraoperative angiogram and/or catheter exchange without sacrificing intraluminal access.

Although numerous embodiments of the invention have been described and discussed above, it will be apparent to those skilled in the art that variations may be made in these embodiments without departing from the scope of the invention. For example, it should be understood that the advantages associated with the use of a radially expandable inner member in the construction of catheters is not limited to an inner member that spans the confines of the balloon component of the catheter. For example, the use of a radially expandable inner member that extends the length of the distal aspect of the catheter, in conjunction with a guidewire of non-uniform profile, can be used to construct an entirely separable angioplasty catheter/guidewire system with a lower distal shaft profile and superior hydraulic performance characteristics relative to the prior art. The scope of our invention may be determined from the following claims.

What is claimed is:

1. A dilatation balloon catheter/guidewire system, comprising:
    an outer member comprising a tubular catheter shaft and a balloon secured to the distal end of said tubular catheter shaft;
    an inner tubular member extending through said balloon and secured to said outer member proximally and distally relative to said balloon; and
    a guidewire extending through said tubular catheter shaft and said inner tubular member, said guidewire containing at least a first section and a second section proximal to, and of larger diameter than, said first section;
    said inner tubular member being:
    non-axially-collapsible and thereby maintaining said balloon in an axially extended condition, and resiliently radially expandable from a reduced-diameter condition sufficiently wide to receive said first section of said guidewire but not said second section, to an expanded-diameter condition sufficiently wide to receive said second section.

2. A dilatation balloon catheter/guidewire system in accordance with claim 1 in which said inner tubular member is fluid-impermeable.

3. A dilatation balloon catheter/guidewire system in accordance with claim 1 in which said tubular catheter shaft defines first and second lumens, said first lumen communicating with said balloon and said second lumen communicating with said inner tubular member, and said inner tubular member is fluid-impermeable.

4. A dilatation balloon catheter/guidewire system in accordance with claim 1 in which said inner tubular member is comprised of first and second tubular submembers, one of said first nd second tubular submembers disposed inside of the other, said first tubular submember being axially compressible and fluid-impermeable, and said second tubular submember being non-axially-compressible and fluid-permeable.

5. A dilatation balloon catheter/guidewire system in accordance with claim 4 in which said first tubular submember is of larger diameter than said second tubular submember and disposed inside said second tubular submember, said first tubular submember being foldable and said second tubular submember containing an axial slit capable of being spread open to accommodate radial expansion of said second tubular submember.

6. A dilatation balloon catheter/guidewire system in accordance with claim 4 in which said first tubular submember is resiliently expandable and disposed inside said second tubular submember, said second tubular submember containing an axial slit capable of being spread open to accommodate radial expansion of said second tubular submember.

7. A dilatation balloon catheter/guidewire system in accordance with claim 4 in which said first tubular submember is resiliently expandable and disposed outside said second tubular submember, said second tubular submember containing an axial slit capable of being spread open to accommodate said second section of said guidewire and thereby expand said first tubular submember.

8. A dilatation balloon catheter/guidewire system in accordance with claim 4 in which said first tubular submember is resiliently expandable and said second tubular submember contains a plurality of axial slits shorter in length than said balloon and capable of being spread open to accommodate radial expansion of said second tubular submember.

9. A dilatation balloon catheter/guidewire system in accordance with claim 1 in which said inner tubular member is comprised of first and second tubular submembers, one of said first and second tubular submembers disposed inside the other, said first tubular submember being axially compressible and fluid-impermeable, and said second tubular submember formed of a strip of non-axially-compressible material curved into a tube with longitudinal edges overlapping.

10. A dilatation balloon catheter/guidewire system in accordance with claim 9 in which said first tubular submember is resiliently expandable.

11. A dilatation balloon catheter/guidewire system in accordance with claim 9 in which said first tubular submember is disposed inside said second tubular submember.

12. A dilatation balloon catheter/guidewire system in accordance with claim 9 in which said first tubular submember is disposed outside said second tubular submember.

13. A dilatation balloon catheter/guidewire system in accordance with claim 1 in which said inner tubular member is a single tube of resilient non-axially-collapsible fluid-impermeable material containing an axial fold capable of being opened by internal outward force to achieve said expanded-diameter condition.

* * * * *